United States Patent [19]

Ledouble et al.

[11] 4,309,360
[45] Jan. 5, 1982

[54] PROCESS FOR THE PRODUCTION OF BIS-[O-(1-ALKYLTHIOETHYLIMINO)-N-METHYLCARBAMYL]N,N'-SULFIDES

[75] Inventors: Jean-Pierre Ledouble, Rosenau, France; Klaus Müller, Reinach, Switzerland

[73] Assignee: Ciba-Geigy Corporation, Ardsley, N.Y.

[21] Appl. No.: 156,965

[22] Filed: Jun. 6, 1980

[30] Foreign Application Priority Data

Jun. 18, 1979 [CH] Switzerland .................. 5670/79

[51] Int. Cl.³ .................. C07C 119/18; A01N 37/18
[52] U.S. Cl. .................. 260/453.1; 424/298
[58] Field of Search .................. 260/453 RW, 453.1

[56] References Cited

U.S. PATENT DOCUMENTS

4,004,031  1/1977  Drabek .................. 424/298

Primary Examiner—John M. Ford
Assistant Examiner—Robert C. Whittenbaugh
Attorney, Agent, or Firm—Karl F. Jorda

[57] ABSTRACT

A process for the production of bis-[O-(1-alkylthioethylimino)-N-methylcarbamyl]-N,N-sulfides of the formula I

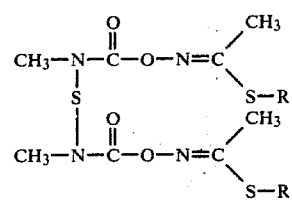

wherein R is a straight-chain or branched alkyl group of 1 to 5 carbon atoms, by reacting a O-(1-alkylthioethylimino)-N-methylcarbamate of the formula

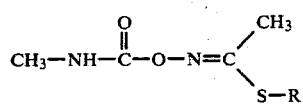

wherein R is as defined above, in the presence of a base, with sulfur dichloride or sulfur monochloride in an inert solvent, which process comprises carrying out said reaction in the presence of 0.01 to 0.5 mole of a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, per mole of O-(1-alkylthioethylimino)-N-methylcarbamate of the formula II.

The bis-[O-(1-alkylthioethylimino)-N-methylcarbamyl]-N,N'-sulfides of the above formula possess insecticidal properties and are suitable in particular for controlling pests of cotton plants and bluebottles.

11 Claims, No Drawings

PROCESS FOR THE PRODUCTION OF BIS-[O-(1-ALKYLTHIOETHYLIMINO)-N-METHYLCARBAMYL]N,N'-SULFIDES

The present invention relates to a process for the production of bis-[O-(1-alkylthioethylimino)-N-methylcarbamyl]-N,N'-sulfides of the formula

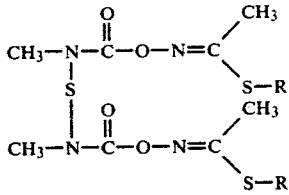

wherein R is a straight-chain or branched alkyl group of 1 to 5 carbon atoms, by reacting a O-(1-alkylthioethylimino)-N-methylcarbamate of the formula

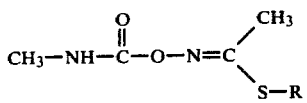

wherein R is as defined above, in the presence of a base, with sulfur dichloride or sulfur monochloride.

The bis-[O-(1-alkylthioethylimino)-N-methylcarbamyl]-N,N'-sulfides of the formula I possess insecticidal properties and are useful in particular for controlling pests of cotton plants and bluebottles (*Lucilia sericata*).

It is already known from U.S. Pat. No. 4,004,031 to obtain the bis-[O-(1-alkylthioethylimino)-N-methylcarbamyl] N,N'-sulfides of the formula I by reaction of a O-(1-alkylthioethylimino)-N-methylcarbamate of the formula II in an inert solvent and in the presence of a base, in the temperature range from −10° to 100° C., with sulfur dichloride or sulfur monochloride. As suitable inert solvents for this reaction, mention is made of ethers, aliphatic and aromatic hydrocarbons and ketones, while suitable bases are in particular tertiary amines such as trialkylamines, pyridines, and N,N-dialkylanilines. The drawback of this method is that the reaction does not proceed uniformly when using the above solvents, resulting in a diminution of the yield and quality of the product. In addition, lengthy reaction times are necessary.

It has now been found that the above disadvantages can be overcome by carrying out the reaction of the O-(1-alkylthioethylimino)-N-methylcarbamate of the formula II with sulfur dichloride or sulfur monochloride, in the presence of 0.01 to 0.5 mole of a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, per mole of O-(1-alkylthioethylimino)-N-methylcarbamate of the formula II.

Especially good results are obtained by carrying out the reaction of the O-(1-alkylthioethylimino)-N-methylcarbamate of the formula II with sulfur dichloride or sulfur monochloride in the presence of N,N-dimethyl formamide.

In a preferred embodiment of the process of this invention, the reaction of a O-(1-alkylthioethylimino)-N-methylcarbamate of the formula II with sulfur dichloride or sulfur monochloride is carried out in the presence of 0.05 to 0.2 mole of a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, per mole of O-(1-alkylthioethylimino)-N-methylcarbamate of the formula II.

Inert solvents in which the process of the present invention can be carried out are aliphatic and aromatic hydrocarbons such as hexane, cyclohexane, benzene, p-xylene and mesitylene, halogenated hydrocarbons such as methylene chloride, chloroform, carbon tetrachloride, tetrachloroethylene and 1,1,2-trifluoro-1,2,2-trichloroethane, and ethers such as diethyl ether, tetrahydrofurane and dioxane. Preferred solvents are 1,1,2-trifluoro-1,2,2,-trichloroethane and p-xylene. The solvents specified above are advantageously employed in amounts of 500 to 1000 ml, preferably 500 to 700 ml, per mole of O-(1-alkylthioethylimino)-N-methylcarbamate of the formula II.

Suitable bases are tertiary amines such as pyridine, alkylpyridines such as picoline and lutidine, and N,N-dialkylanilines which are substituted in the para-position by halogen, alkyl and alkoxy. The preferred base is pyridine.

The above bases can be employed in stoichiometric amount or in an excess of up to 100%. It is preferred to employ an excess of 50%, based on the stoichiometric amount.

The process of the present invention is carried out in the temperature range from −10° to 50° C., with the preferred range being from 0° to 30° C. The reaction usually takes less than 5 hours and in most cases is complete after 1 to 2 hours.

The process of the invention is advantageously carried out by initially adding the base, preferably pyridine, with cooling, to a ready prepared mixture of solvent and sulfur dichloride or sulfur monochloride, and then adding the O-(1-alkylthioethylimino)-N-methylcarbamate of the formula II and finally a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, preferably N,N-dimethyl formamide, and keeping the reaction mixture for 1 to 2 hours at a temperature in the range from 0° to 30° C.

The starting O-(1-alkylthioethylimino)-N-methylcarbamates of the formula II are known from British patent specification No. 1,138,347. They can be produced e.g. by reaction of acetaldehyde with hydroxylamine to give acetaldoxime, further reaction of the acethydroxyamyl chloride obtained by chlorination of acetaldoxime with alkali alkylmercaptide to give the corresponding 1-alkylthioacetaldoxime, and further reaction of this latter with methyl isocyanate.

The process of the present invention makes it possible to obtain the bis-[O-(1-alkylthioethylimino)-N-methylcarbamyl]-N,N'-sulfides of the formula I in yields between 80 and 90% of theory, while substantially avoiding the formation of undesirable by-products. The final products are obtained in a purity of 95% and can be used without further purification. In addition, the process of this invention makes it possible to shorten the reaction time substantially to less than 5 hours. The process of the invention is therefore most suitable for the production of the insecticidal compounds of the formula I on an industrial scale.

The following Examples illustrate the process of the invention in more detail.

EXAMPLE 1

With cooling, 55 g of pyridine are added dropwise at 5° to 10° C. to a mixture of 31.0 g (0.30 mole) of sulfur dichloride and 285 ml of 1,1,2-trifluoro-1,2,2-trichloroethane (Flugen ® 113). When the addition of pyridine is complete, 75 g (0.046 mole) of O-(1-methylthioethylimino)-N-methylcarbamate and then 3.3 ml of N,N-dimethyl formamide are added at 10° C. The reaction mixture is then stirred for 2 hours at 25°–30° C. and filtered. The product is stirred with water, collected by filtration once more and dried at 40° C. in vacuo, affording 77.6 g of 95% bis-[O-(1-methylthioethylimino)-N-methylcarbamyl]-N,N'-sulfide, corresponding to a yield of 90% of theory, based on O-(1-methylthioethylimino)-N-methylcarbamate.

EXAMPLE 2

31.0 g (0.30 mole) of sulfur dichloride and 75 g (0.46 mole) of o-(1-methylthioethylimino)-N-methylcarbamate are reacted in the presence of 5.6 ml of N,N-dimethyl formamide in 300 ml of p-xylene in accordance with the method described in Example 1, except that the reaction mixture is stirred for 3 hours at 25°–30° C. after addition of the N,N-dimethyl formamide. Yield: 72.6 g (85% of theory, based on O-(1-methylthioethylimino)-N-methylcarbamate) of 95% bis-[O-(methylthioethylimino)-N-methylcarbamyl]-N,N'-sulfide.

What is claimed is:

1. In a process for the production of bis-[O-(1-alkylthioethylimino)-N-methylcarbamyl]-N,N'-sulfides of the formula I

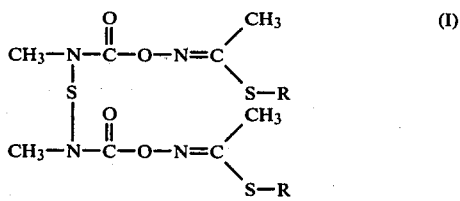

wherein R is a straight-chain or branched alkyl group of 1 to 5 carbon atoms, by reacting a O-(1-alkylthioethylimino)-N-methylcarbamate of the formula

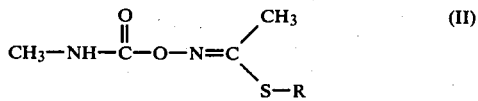

wherein R is as defined above, in the presence of a base, with sulfur dichloride or sulfur monochloride in an inert solvent, the improvement which comprises carrying out said reaction in the presence of 0.01 to 0.5 mole of a catalytic compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, per mole of O-(1-alkylthioethylimino)-N-methylcarbamate of the formula II.

2. A process according to claim 1, wherein the reaction of the O-(1-alkylthioethylimino)-N-methylcarbamate of the formula II with sulfur dichloride or sulfur monochloride is carried out in the presence of N,N-dimethyl formamide.

3. A process according to claim 1, wherein the reaction of an O-(1-alkylthioethylimino)-N-methylcarbamate of the formula II with sulfur dichloride or sulfur monochoride is carried out in the presence of 0.05 to 0.2 mole of a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, per mole of O-(1-alkylthioethylimino)-N-methylcarbamate of the formula II.

4. A process according to claim 1, wherein the inert solvent is an aliphatic or aromatic hydrocarbon, a halogenated hydrocarbon or an ether.

5. A process according to claim 1, wherein the solvent is 1,1,2-trifluoro-1,2,2-trichloroethane or p-xylene.

6. A process according to claim 1, wherein the base is a tertiary amine.

7. A process according to claim 1, wherein the base is pyridine.

8. A process according to claim 1, wherein the base is employed in an excess of 50%, based on the stoichiometric amount.

9. A process according to claim 1, wherein the reaction of a O-(1-alkylthioethylimino)-N-methylcarbamate of the formula II with sulfur dichloride or sulfur monochloride is carried out in the temperature range from −10° to +50° C.

10. A process according to claim 1, wherein the reaction of a O-(1-alkylthioethylimino)-N-methylcarbamate of the formula II with sulfur dichloride or sulfur monochloride is carried out in the temperature range from 0° to +30° C.

11. A process according to claim 1, which comprises carrying out the reaction of a O-(1-alkylthioethylimino)-N-methylcarbamate of the formula II with sulfur dichloride or sulfur monochloride by initially adding the base, with cooling, to a ready prepared mixture of solvent and sulfur dichloride or sulfur monochloride, and then adding the O-(1-alkylthioethylimino)-N-methylcarbamate of the formula II and finally a compound selected from the group consisting of N,N-dialkylformamides, each containing 1 to 4 carbon atoms in the alkyl moieties, N-methylpyrrolidone, dimethyl sulfoxide, phosphoric acid tris-N,N-dimethylamide and tetramethyl urea, and keeping the reaction mixture for 1 to 2 hours at a temperature in the range from 0° to 30° C.

* * * * *